(12) United States Patent
Tsai et al.

(10) Patent No.: US 10,151,572 B1
(45) Date of Patent: Dec. 11, 2018

(54) OPTICAL SECTIONING APPARATUS USING ADVANCED OPTICAL INTERFERENCE MICROSCOPY

(71) Applicant: AcuSolutions Inc., Apia (WS)

(72) Inventors: Chien-Chung Tsai, Taipei (TW); Kuang-Yu Hsu, Taipei (TW)

(73) Assignee: ACUSOLUTIONS INC., Apia (WS)

( * ) Notice: Subject to any disclaimer, the term of this patent is extended or adjusted under 35 U.S.C. 154(b) by 0 days.

(21) Appl. No.: 15/679,478

(22) Filed: Aug. 17, 2017

(30) Foreign Application Priority Data

Jun. 5, 2017 (TW) .............................. 106118559 A

(51) Int. Cl.
| | | |
|---|---|---|
| *G01B 9/02* | (2006.01) | |
| *H04N 7/18* | (2006.01) | |
| *A61B 5/00* | (2006.01) | |
| *G02B 21/00* | (2006.01) | |

(52) U.S. Cl.
CPC .......... *G01B 9/0203* (2013.01); *A61B 5/0066* (2013.01); *G01B 9/02041* (2013.01); *G01B 9/02057* (2013.01); *G01B 9/02065* (2013.01); *G01B 9/02091* (2013.01); *G02B 21/0056* (2013.01); *G02B 21/0076* (2013.01); *H04N 7/18* (2013.01); *G01B 2290/60* (2013.01)

(58) Field of Classification Search
CPC ............ G02B 21/0056; G02B 21/0076; G01B 9/0203; G01B 9/02041; G01B 9/02057; G01B 9/02065; G01B 9/02091; G01B 2290/60; A61B 5/0066
See application file for complete search history.

(56) References Cited

U.S. PATENT DOCUMENTS

| | | | | |
|---|---|---|---|---|
| RE36,529 E | * | 1/2000 | Lewis .................. | G01J 3/2823 250/339.02 |
| 7,978,336 B2 | * | 7/2011 | Mann ..................... | G01B 9/021 356/485 |
| 8,248,614 B2 | * | 8/2012 | Mann ..................... | G01B 9/021 356/485 |
| 9,185,357 B2 | | 11/2015 | Boccara et al. | |
| 2008/0085550 A1 | * | 4/2008 | Werner ............... | G01N 15/1475 435/287.2 |
| 2010/0224796 A1 | * | 9/2010 | Mertz ................ | G02B 21/0056 250/459.1 |
| 2011/0261367 A1 | * | 10/2011 | Gmitro ................ | A61B 5/0066 356/479 |

(Continued)

*Primary Examiner* — Shawn Decenzo
(74) *Attorney, Agent, or Firm* — Guice Patents PLLC

(57) ABSTRACT

An optical sectioning apparatus using optical interference microscopy and fluorescence microscopy, including: a beam splitter capable of splitting an incident light beam into a reflected light beam and a transmitted light beam; a wide band light source for providing the incident light beam; a reference arm unit for making the transmitted light beam travel a round trip along an adjustable optical path; a short wavelength light source; a first dichroic splitter, with a first side facing the short wavelength light source and a third side facing the beam splitter, being capable of providing a light-blocking effect on wavelengths shorter than a preset wavelength; an objective lens, with a collimated side facing a second side of the first dichroic splitter; a sample carrier unit facing a focal side of the objective lens; and a projection lens and a sensor units for receiving an output light beam.

11 Claims, 8 Drawing Sheets

(56) References Cited

U.S. PATENT DOCUMENTS

| | | | |
|---|---|---|---|
| 2012/0069344 A1* | 3/2012 | Liu | G01B 9/04 356/450 |
| 2012/0200694 A1* | 8/2012 | Garsha | G01N 21/6456 348/79 |
| 2013/0182096 A1* | 7/2013 | Boccara | A61B 5/0066 348/79 |
| 2016/0078309 A1* | 3/2016 | Feldman | G01B 9/0203 382/131 |

* cited by examiner

OPTICAL SECTIONING APPARATUS USING ADVANCED OPTICAL INTERFERENCE MICROSCOPY

BACKGROUND OF THE INVENTION

Field of the Invention

The present invention relates to an optical sectioning apparatus, especially to an optical sectioning apparatus using optical interference microscopy and fluorescence microscopy.

Description of the Related Art

In conventional tumor surgery, it takes a lot of time for a pathologist to examine a frozen section to determine if a tumor is cleanly removed. As a result, when the time allowed for the surgery is shorter than the time needed for the pathologist to complete the assessment of intraoperative pathological margin, the tumor cannot be guaranteed to be cleanly removed.

During the process of preparing a frozen section of a sample, if the sample contains much water, a formed crystal ice structure will cause a damage to the tissue structure of the sample; and if the sample contains much fat, the fat will still be not frozen at temperatures around −20° C. where the other tissues are already frozen, and is therefore easy to slip off from the frozen section to cause an artifact to the frozen section.

OCT (optical coherence tomography) is a newly developed optical imaging technology, which utilizes an operational principle similar to that of the supersonic imaging technology but has a higher resolution than the supersonic imaging technology. OCT mainly utilizes the phenomena that different tissues of a sample have different responses with regard to light reflection, light absorption, and light scattering and makes use of an optical interference methodology to form an image of the sample for diagnosis. Since OCT can be performed by directly scanning a sample at room temperature without the need of including a freezing procedure and a slicing procedure, morphological artifacts induced by slicing a frozen sample containing much water or fat can be prevented, the completeness of the sample can be maintained to ensure the accuracy of a pathological assessment, the surgery time can be shortened, and surgery effect can be improved. However, since traditional optical microscopy usually has a wide depth of focus, a sample needs to undergo a real sectioning procedure to provide sections of a depth of 4-5 μm, so as to avoid overlapping of tissue images of different depths, and thereby to derive a clear image.

To solve the foregoing problems, the U.S. Pat. No. 9,185,357 B2 discloses an optical tissue sectioning apparatus using full-field optical coherence tomography, which includes a full-field imaging interferometer and an optical sectioning imaging system. This optical tissue sectioning apparatus uses the interferometer to solve the problem resulting from the wide depth of focus by directly deriving the image from the sample, which has a resolution as precise as less than 1 μm both laterally and vertically, getting rid of the need of a fixation process, which includes a freezing procedure, a paraffin-embadded procedure, and a real sectioning procedure.

Besides, as a conventional H&E stain section uses hematoxylin to color the nuclei bluish violet and uses eosin to color cytoplasm pink, the nuclei will also be represented in bluish violet in a derived image, and the details (such as the nucleolus or heterochromatin) of each of the nuclei will be undistinguishable in the derived image. Therefore, U.S. Pat. No. 9,185,357 B2 adopts a fluorescent staining approach to exhibit an image of the details of nuclei to fulfill the need of pathology inspection.

However, there is still room for improvement in the performance of U.S. Pat. No. 9,185,357 B2, for example: (1) a short-wavelength light beam (such as UV light beam) will be attenuated by a beam-splitting film of the beam splitter by 60-90%; (2) the antireflection film of the beam splitter generally has a low transmission rate for a UV band of wavelengths shorter than 400 nm. Due to these two disadvantages, a fluorescent signal out of a sample will very weak. To ensure the strength of a fluorescent signal, shorten exposure time, and speed up an image taking process, a novel optical sectioning apparatus is needed.

SUMMARY OF THE INVENTION

One objective of the present invention is to disclose an optical sectioning apparatus, in which a first dichroic splitter is disposed between a beam splitter and a first objective lens to block a short-wavelength light beam and thereby increase a relative strength of a fluorescent signal, shorten an exposure time, and speed up taking images.

Another objective of the present invention is to disclose an optical sectioning apparatus, in which a first dichroic splitter will filter out a short-wavelength light beam so that when a fluorescent light beam emitted from a sample passes through the first dichroic splitter, the fluorescent light beam will have a good relative strength to shorten an exposure time and speed up taking images.

Still another objective of the present invention is to disclose an optical sectioning apparatus, in which a sensor unit has a long-wavelength-pass filter to further filter out a short-wavelength light beam to increase the relative strength of a fluorescent signal, and thereby shorten an exposure time and speed up taking images.

To attain the foregoing objectives, an optical sectioning apparatus using optical interference microscopy and fluorescence microscopy is proposed, including:

a beam splitter, having a first side, a second side, a third side, and a fourth side, and being capable of splitting an incident light beam entering received from the first side into a reflected light beam traveling out the second side and a transmitted light beam traveling out the third side;

a wide band light source apparatus for generating a wide band light beam to be incident on the first side of the beam splitter;

a reference arm unit, used to make the transmitted light beam travel a round trip along an adjustable optical path and then return to the beam splitter;

a short wavelength light source apparatus for generating a short wavelength light beam;

a first dichroic splitter, having a first side, a second side, and a third side, with the first side facing the short wavelength light source apparatus, the third side facing the second side of the beam splitter, and being capable of providing a light-blocking effect on a band of wavelengths shorter than a preset wavelength, and the short wavelength light beam having a wavelength shorter than the preset wavelength;

a first objective lens, having a collimated side and a focal side, with the collimated side facing the second side of the first dichroic splitter;

a sample carrier unit facing the focal side of the first objective lens and being used for carrying a sample stained with a fluorescent dye;

a projection lens, having a light entrance side and a light exit side, with the light entrance side facing the fourth side of the beam splitter; and a sensor unit facing the light exit side of the projection lens.

In one embodiment, the reference arm unit includes: an optical path delay unit, having a first side and a second side, with the first side facing the third side of the beam splitter; a second objective lens, having a collimated side and a focal side, with the collimated side facing the second side of the optical path delay unit; and a reflective mirror, facing the focal side of the second objective lens and used for reflecting the transmitted light beam, wherein the optical path delay unit is used for adjusting the adjustable optical path so that the adjustable optical path and a sample arm optical path have an optical path difference less than a coherent length, with the sample arm optical path being formed by the sample carrier unit, the first objective lens, and the first dichroic splitter.

In one embodiment, both the wide band light source apparatus and the short wavelength light source apparatus are implemented with a light source, or a combination of a light source and a grating, or a combination of a light source, a grating, and an tilt-adjustable reflective mirror, or a plurality of parallel LED stripes.

In one embodiment, the sample carrier unit further includes a white light source to provide a proper intensity of white light to pass through the first objective lens, the white light source including a white-light LED, a laser-diode-pumped crystal rod, a laser-diode-pumped crystal fiber, a white-light halogen lamp, or a tungsten lamp.

In one embodiment, the sensor unit includes a second dichroic splitter, a two-dimensional color sensing device, a long wavelength pass filter, and a two-dimensional monochrome sensing device, in which the second dichroic splitter has a first side, a second side, and a third side, with the first side facing the projection lens, and the second dichroic splitter is used to reflect a fluorescent light beam and a white light beam to and through the third side to form an image on the two-dimensional color sensing device, and to transmit a wide band light beam through the second side to form an image on the two-dimensional monochrome sensing device.

In one embodiment, the sensor unit includes a flip-type reflective mirror, a two-dimensional color sensing device, a long wavelength pass filter, and a two-dimensional monochrome sensing device, in which the flip-type reflective mirror has a flip-on state to allow a white light beam to form an image on the two-dimensional color sensing device, and has a flip-off state to allow a wide band light beam and a fluorescent light beam to form an image on the two-dimensional monochrome sensing device, and the long wavelength pass filter can be disposed between the projection lens and the flip-type reflective mirror, or be disposed between the projection lens and the second dichroic splitter, or be disposed between the flip-type reflective mirror and the two-dimensional monochrome sensing device, or be disposed between the second dichroic splitter and the two-dimensional monochrome sensing device.

In one embodiment, the wide band light beam has a wavelength range of 470 nm-800 nm, the short wavelength light beam has a wavelength range of 365 nm-460 nm, the beam splitter has an operating wavelength range of 400 nm-800 nm, and both the first dichroic splitter and the long wavelength pass filter have a cut-off wavelength range of 400 nm-470 nm.

In one embodiment, the wide band light beam has a wavelength range of 650 nm-1000 nm, the short wavelength light beam has a wavelength range of 365 nm-630 nm, the beam splitter has an operating wavelength range of 400 nm-1000 nm, and all the first dichroic splitter, the second dichroic splitter, and the long wavelength pass filter have a cut-off wavelength range of 400 nm-650 nm.

In one embodiment, a first polarizer is disposed between the wide band light source apparatus and the beam splitter, a second polarizer is disposed in front of the two-dimensional monochrome sensing device, a first quarter-wave plate is disposed between the first objective lens and the first dichroic splitter, and a second quarter-wave plate is disposed between the optical path delay unit and the second objective lens, wherein the first polarizer has a first polarization direction, the second polarizer has a second polarization direction orthogonal to the first polarization direction, the first quarter-wave plate has a first optical axis direction, the second quarter-wave plate has a second optical axis direction, and both the first optical axis direction and the second optical axis direction are disposed within a range formed by the first polarization direction and the second polarization direction to enhance an interference effect and promote an imaging quality.

In one embodiment, an information processing apparatus is used to perform an image processing process.

In one embodiment, the reference arm unit further includes an axial motion platform, and the sample carrier unit further includes a 3-D motion platform, so that by using the axial motion platform to move the second objective lens and the reflective mirror of the reference arm unit, using the 3-D motion platform to move the sample stained with a fluorescent dye, and adjusting the optical path delay unit, the information processing apparatus can derive a 3-D image of the sample accordingly.

To make it easier for our examiner to understand the objective of the invention, its structure, innovative features, and performance, we use preferred embodiments together with the accompanying drawings for the detailed description of the invention.

DETAILED DESCRIPTION OF THE PREFERRED EMBODIMENTS

Figure 1:
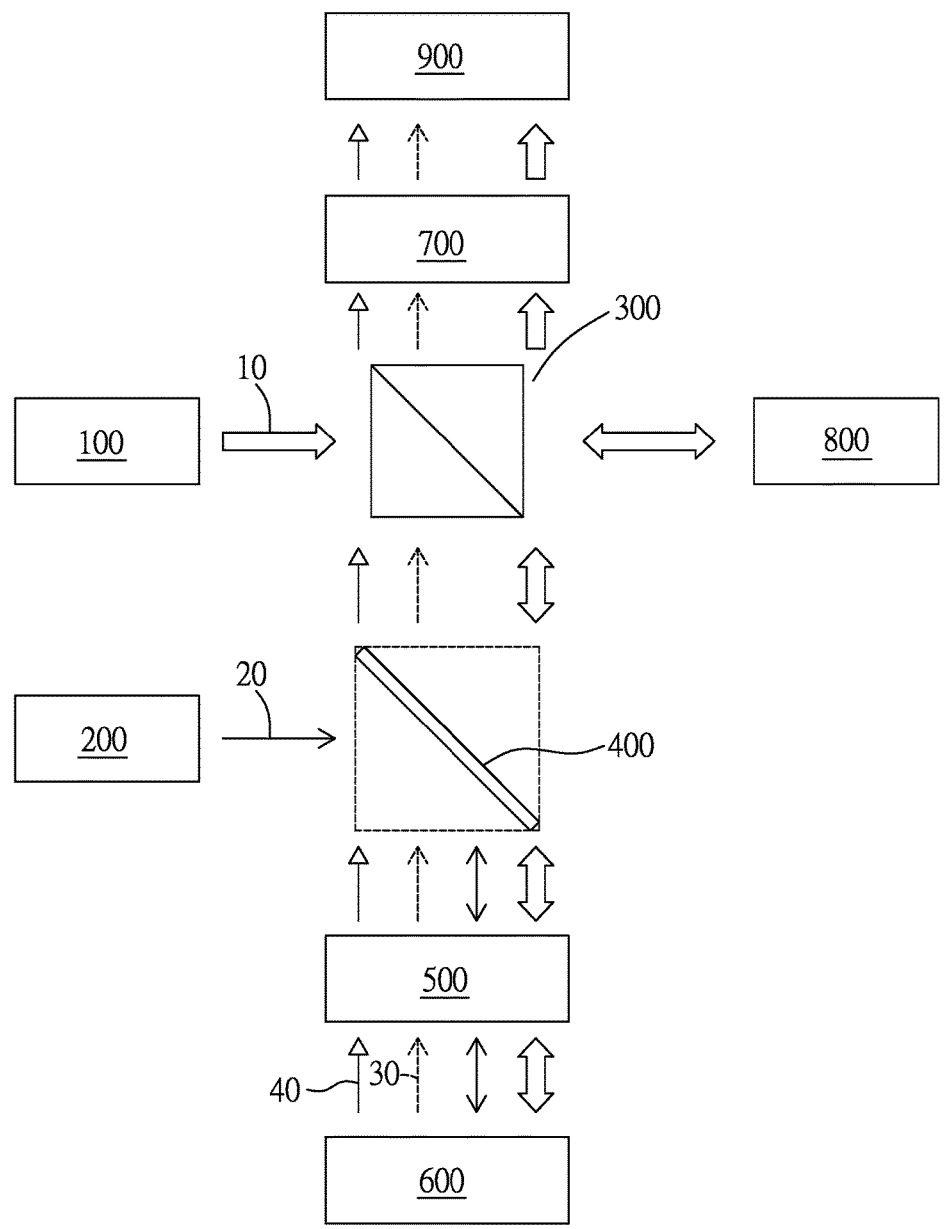
FIG. 1 illustrates a block diagram of an optical sectioning apparatus using optical interference microscopy and fluorescence microscopy according to one embodiment of the present invention.
Figure 2:
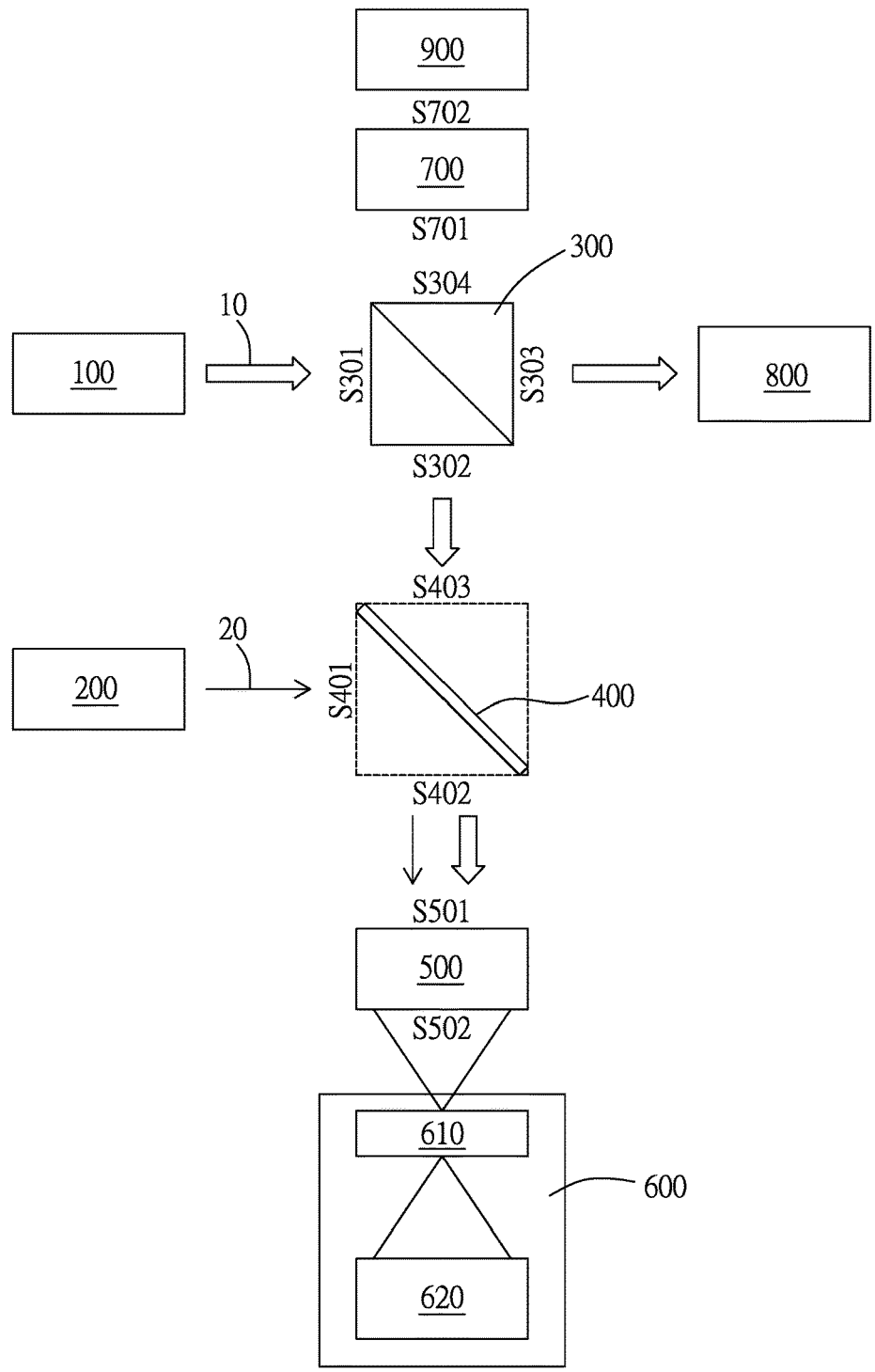
FIG. 2 illustrates a beam splitting operation and a focusing operation of the optical sectioning apparatus of FIG. 1.

Please refer to FIG. 1-2, in which, FIG. 1 illustrates a block diagram of an optical sectioning apparatus using optical interference microscopy and fluorescence microscopy according to one embodiment of the present invention, and FIG. 2 illustrates a beam splitting operation and a focusing operation of the optical sectioning apparatus in FIG. 1.

As illustrated in the figures, the optical sectioning apparatus using optical interference microscopy and fluorescence microscopy includes: a wide band light source apparatus 100, a short wavelength light source apparatus 200, a beam splitter 300, a first dichroic splitter 400, a first objective lens 500, a sample carrier unit 600, a projection lens 700, a reference arm unit 800, and a sensor unit 900.

The wide band light source apparatus 100 is used to generate a wide band light beam 10 (indicated by a hollow arrow); the short wavelength light source apparatus 200 is used to generate a short wavelength light beam 20 (indicated by a solid arrow); the sample carrier unit 600 is used to carry a sample 610 stained with a fluorescent dye, which will emit a fluorescent light beam 30 (indicated by a dashed line arrow) when the short wavelength light beam 20 is incident on it; and the sample carrier unit 600 further includes a white light source 620 to provide a white light beam 40 (indicated by a hollow arrowhead) having a proper intensity to pass through the first objective lens 500.

The beam splitter 300 has a first side S301, a second side S302, a third side S303, and a fourth side S304. The wide band light source apparatus 100 is used for generating the wide band light beam 10 to be incident on the first side S301 of the beam splitter 300 and divided by the beam splitter 300 into a reflected wide band light beam traveling out the second side S302, and a transmitted wide band light beam traveling out the third side S303.

The short wavelength light source apparatus 200 is used to generate the short wavelength light beam 20. The first dichroic splitter 400 has a first side S401, a second side S402, and a third side S403, with the first side S401 facing the short wavelength light source apparatus 200 and reflecting the short wavelength light beam 20, and with the third side S403 facing the second side S302 of the beam splitter 300 to transmit a branch of the wide band light beam 10 from the beam splitter 300 through the second side S402.

The first objective lens 500 has a collimated side S501 and a focal side S502, wherein, the collimated side S501 facing the second side S402 of the first dichroic splitter 400. The sample carrier unit 600 faces the focusing side S502 of the first objective lens 500 and is used to carry the sample 610 stained with a fluorescent dye. Besides, the sample carrier unit 600, the first objective lens 500, and the first dichroic splitter 400 together form a sample arm optical path.

The projection lens 700 has a light entrance side S701 and a light exit side S702, with the light entrance side S701 facing the fourth side S304 of the beam splitter 300. The sensor unit 900 faces the light exit side S702 of the projection lens 700. Besides, the white light source 620 includes a white-light LED, a white-light halogen lamp, or a tungsten lamp, etc.; the first objective lens 500 has an operating wavelength range of 350 nm-1000 nm; and both the wide band light source apparatus 100 and the short wavelength light source apparatus 200 can be implemented with a light source, or a combination of a light source and a grating, or a combination of a light source, a grating, and a tilt-adjustable reflective mirror, or a plurality of parallel LED stripes (all not shown in the figure). As the light source, the grating, the tilt-adjustable reflective mirror, and the parallel LED stripes are already known in prior art, they will not be further addressed.

Figure 3:
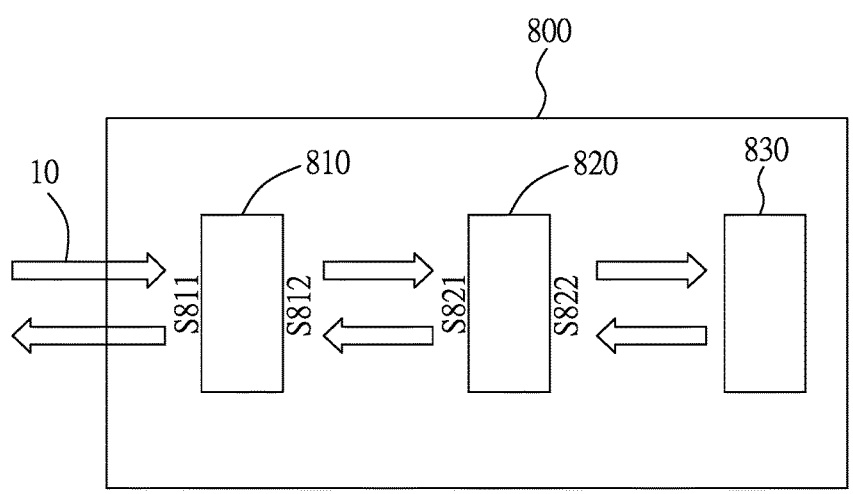
FIG. 3 illustrates a block diagram of a reference arm unit of FIG. 1 according to one embodiment of the present invention.

Please refer to FIG. 3, which illustrates a block diagram of a reference arm unit of FIG. 1 according to one embodiment of the present invention.

As illustrated in FIG. 3, the reference arm unit 800 includes: an optical path delay unit 810, a second objective lens 820, and a reflective mirror 830.

The optical path delay unit 810, the second objective lens 820, and the reflective mirror 830 together form an adjustable optical path, and the reference arm unit 800 is used to make a branch of the wide band light beam 10 travel a round trip along the adjustable optical path and then return to the beam splitter 300 (not shown in this figure).

The optical path delay unit 810 has a first side S811 and a second side S812, with the first side S811 facing the third side S303 of the beam splitter 300 (not shown in this figure); the second objective lens 820 has a collimated side S821 and a focal side S822, with the collimated side S821 facing the second side S812 of the optical path delay unit 810; and the reflective mirror 830 faces the focusing side S822 of the second objective lens 820 for reflecting the branch of the wide band light beam 10. In addition, the second objective lens 820 can have an operating wavelength range of 350-1000 nm.

The optical path delay unit 810 can use a reflective mirror to help make the adjustable optical path and the sample arm optical path have an optical path difference less than a coherent length by changing a displacement of the reflective mirror. One or more continuous interference carrier waves can be continuously recorded by a two-dimensional monochrome sensing device 940, and a plurality of recorded intensity values then undergo a root-mean-square calculation and an averaging calculation to produce an en-face interference intensity image, wherein the continuous interference carrier wave can also be generated by a 3-D motion platform 630, of which the principle is known in prior art, so it will not further addressed.

Figure 4:
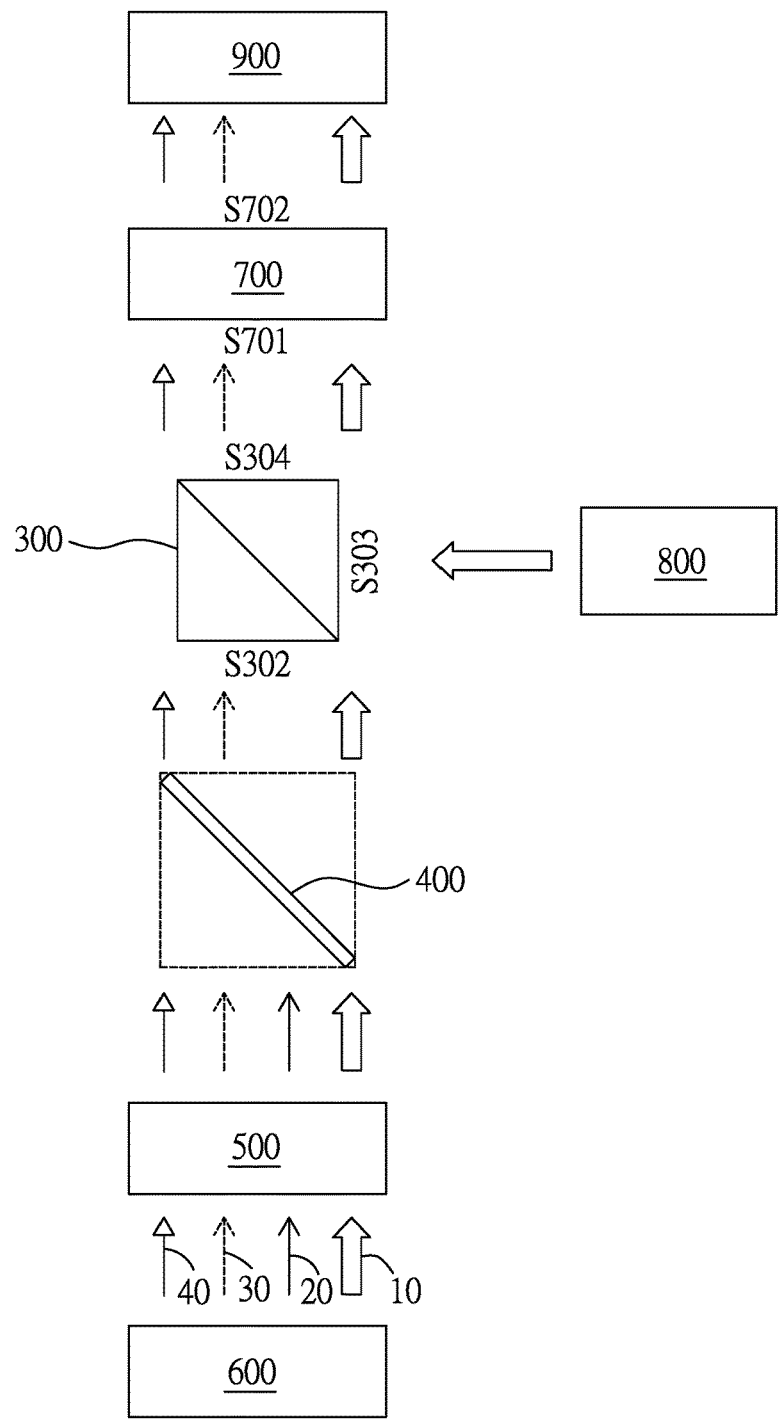
FIG. 4 illustrates a beam combining operation and an image projecting operation of the optical sectioning apparatus of FIG. 1.

Please refer to FIG. 4, which illustrates a beam combining operation and an image projecting operation of the optical sectioning apparatus of FIG. 1.

As illustrated in FIG. 4, the sample carrier unit 600 is capable of reflecting the short wavelength light beam 20 and a branch of the wide band light beam 10, and the sample 610 stained with a fluorescent dye (not shown in this figure) will emit the fluorescent light beam 30 when hit by the short wavelength light beam 20. In addition, the white light source 620 (not shown in this figure) of the sample carrier unit 600 will emit the white light beam 40.

The first dichroic splitter 400 is used to block a band of wavelengths shorter than a preset wavelength, and the short wavelength light beam 20 has a wavelength shorter than the preset wavelength, so the short wavelength light beam 20 will be blocked by the first dichroic splitter 400, while the branch of the wide band light beam 10, the fluorescent light beam 30, and the white light beam 40 will pass through the first dichroic splitter 400.

The third side S303 of the beam splitter 300 faces the reference arm unit 800 and is used to reflect the branch of the wide band light beam 10 from the reference arm unit 800 to the fourth side S304, and the second side S302 faces the first dichroic splitter 400 and is used to transmit another branch of the wide band light beam 10, the fluorescent light beam 30, and the white light beam 40 to the fourth side S304.

Since the adjustable optical path and the sample optical path have an optical path difference less than a coherent length, the wideband light beam traveling a round trip along the adjustable optical path will have an optical interference with the wideband light beam traveling a round trip along the sample optical path when they meet each other. Since the interference principle is known in prior art, it will not be addressed further.

The projection lens 700 has a light entrance side S701 and a light exit side S702, with the light entrance side S701 facing the fourth side S304 of the beam splitter 300, and the light exit side S702 being used to transmit a coherent-interference resultant light beam of the wide band light beam 10, the fluorescent light beam 30, and the white light beam 40 to the sensor unit 900.

Figure 5A:
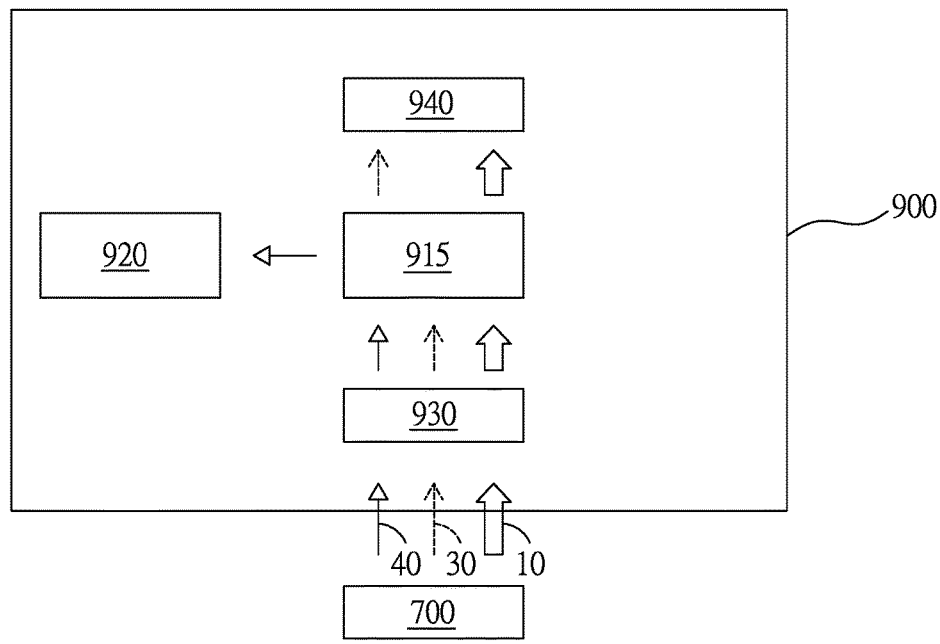
FIG. 5a illustrates a block diagram of a sensor unit of FIG. 1 according to one embodiment of the present invention.
Figure 5B:
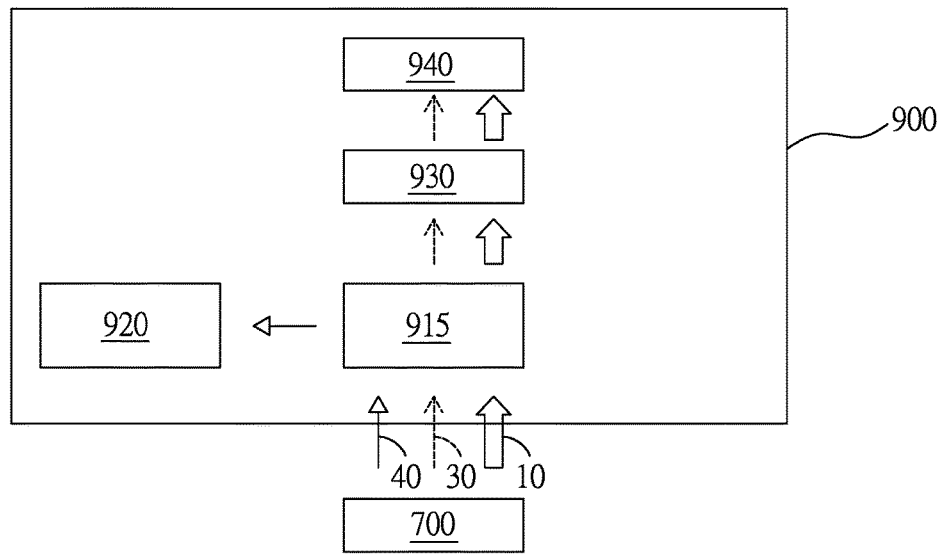
FIG. 5b illustrates a block diagram of a sensor unit of FIG. 1 according to another embodiment of the present invention.

Please refer to FIG. 5a-5b, in which, FIG. 5a illustrates a block diagram of a sensor unit of FIG. 1 according to one embodiment of the present invention and FIG. 5b illustrates a block diagram of a sensor unit of FIG. 1 according to another embodiment of the present invention.

The sensor unit 900 includes a flip-type reflective mirror 915, a two-dimensional color sensing device 920, a long wavelength pass filter 930 and a two-dimensional monochrome sensing device 940.

The long wavelength pass filter 930 is used to further filter out the short wavelength light beam 20 (not shown in the figure), and the flip-type reflective mirror 915 has a flip mount (not shown in the figure) for presenting a flip-on state or a flip-off state. Since the flip-type reflective mirror is known in prior art, it will not be addressed further.

As illustrated in FIG. 5a, the long wavelength pass filter 930 is disposed between the projection lens 700 and the flip-type reflective mirror 915. When the flip-type reflective mirror 915 is in the flip-on state, the white light beam 40 will form an image on the two-dimensional color sensing device 920; when the flip-type reflective mirror 915 is in the flip-off state, the fluorescent light beam 30 and a coherent-interference resultant light beam of the wide band light beam 10 will form an image on the two-dimensional monochrome sensing device 940, respectively.

As illustrated in FIG. 5b, the long wavelength pass filter 930 is disposed between the flip-type reflective mirror 915 and the two-dimensional monochrome sensing device 940. When the flip-type reflective mirror 915 is in the flip-on state, the white light beam 40 will form an image on the two-dimensional color sensing device 920; when the flip-type reflective mirror 915 is in the flip-off state, the fluorescent light beam 30 and a coherent-interference resultant light beam of the wide band light beam 10 will form an image on the two-dimensional monochrome sensing device 940 respectively.

Figure 5C:
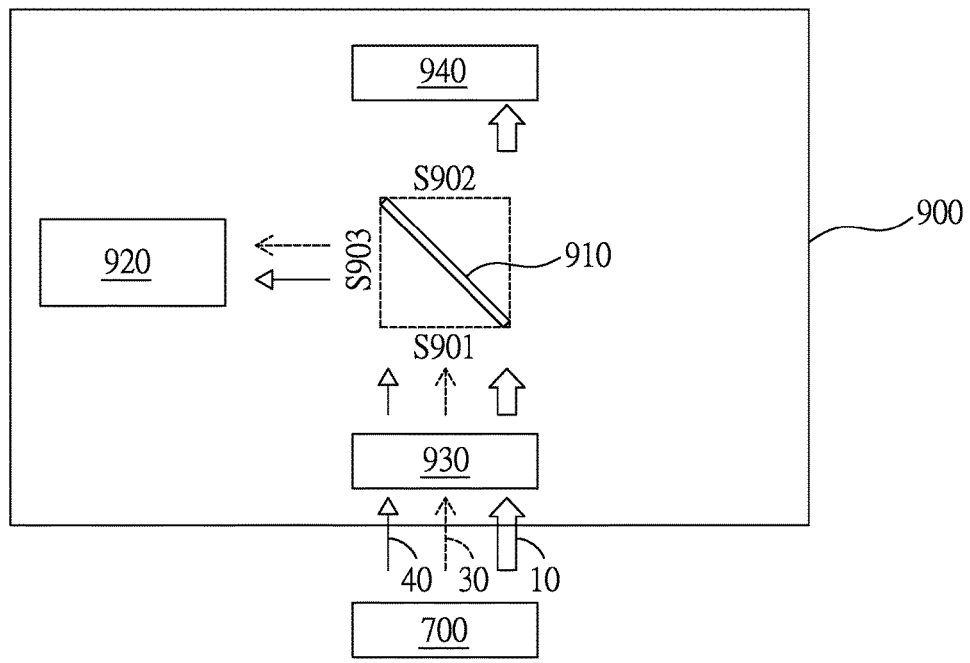
FIG. 5c illustrates a block diagram of a sensor unit of FIG. 1 according to another embodiment of the present invention.
Figure 5D:
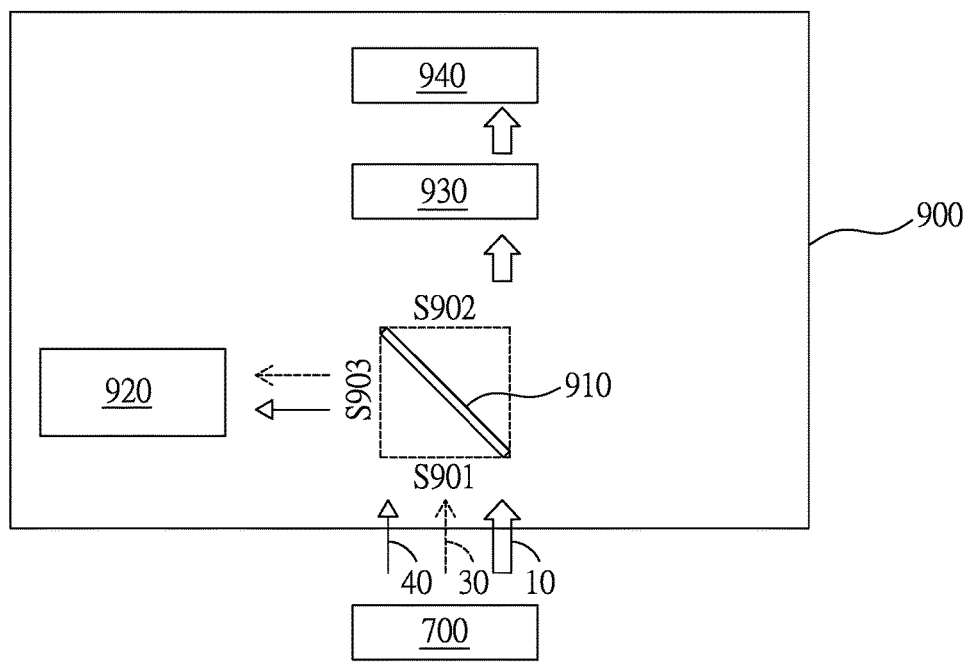
FIG. 5d illustrates a block diagram of a sensor unit of FIG. 1 according to still another embodiment of the present invention.

Please refer to FIG. 5c-5d, in which FIG. 5c illustrates a block diagram of a sensor unit of FIG. 1 according to another embodiment of the present invention, and FIG. 5d illustrates a block diagram of a sensor unit of FIG. 1 according to still another embodiment of the present invention.

The sensor unit 900 includes a second dichroic splitter 910, a two-dimensional color sensing device 920, a long wavelength pass filter 930 and a two-dimensional monochrome sensing device 940, in which the long wavelength pass filter 930 is used to further filter out the short wavelength light beam 20 (not shown in the figure).

As illustrated in FIG. 5c, the long wavelength pass filter 930 is disposed between the projection lens 700 and the second dichroic splitter 910. The second dichroic splitter 910 reflects the fluorescent light beam 30 and the white light beam 40 to the third side S903 to form an image on the two-dimensional color sensing device 920, and transmits a coherent-interference resultant light beam of the wide band light beam 10 through the second side S902 to form an image on the two-dimensional monochrome sensing device 940.

As illustrated in FIG. 5d, the long wavelength pass filter 930 is disposed between the second dichroic splitter 910 and the two-dimensional monochrome sensing device 940. The second dichroic splitter 910 reflects the fluorescent light beam 30 and the white light beam 40 to the third side S903 to form an image on the two-dimensional color sensing device 920, and transmits a coherent-interference resultant light beam of the wide band light beam 10 through the second side S902 to form an image on the two-dimensional monochrome sensing device 940.

When the wide band light beam 10 has a wavelength range of 470 nm-800 nm, the flip-type reflective mirror 915 is required, the short wavelength light beam 20 (not shown in this figure) has a wavelength range of 365 nm-460 nm, the beam splitter 300 (not shown in this figure) has an operating wavelength range of 400 nm-800 nm, and the first dichroic splitter 400 has a cut-off wavelength range of 400 nm-470 nm. When the wide band light beam 10 has a wavelength range of 650 nm-1000 nm, the flip-type reflective mirror 915 or the second dichroic splitter 910 can be adopted, the short wavelength light beam 20 has a wavelength range of 365 nm-630 nm, the beam splitter 300 has an operating wavelength range of 400 nm-1000 nm, and all the first dichroic splitter 400, the second dichroic splitter 910, and the long wavelength pass filter 930 have a cut-off wavelength range of 400 nm-650 nm.

Figure 6:
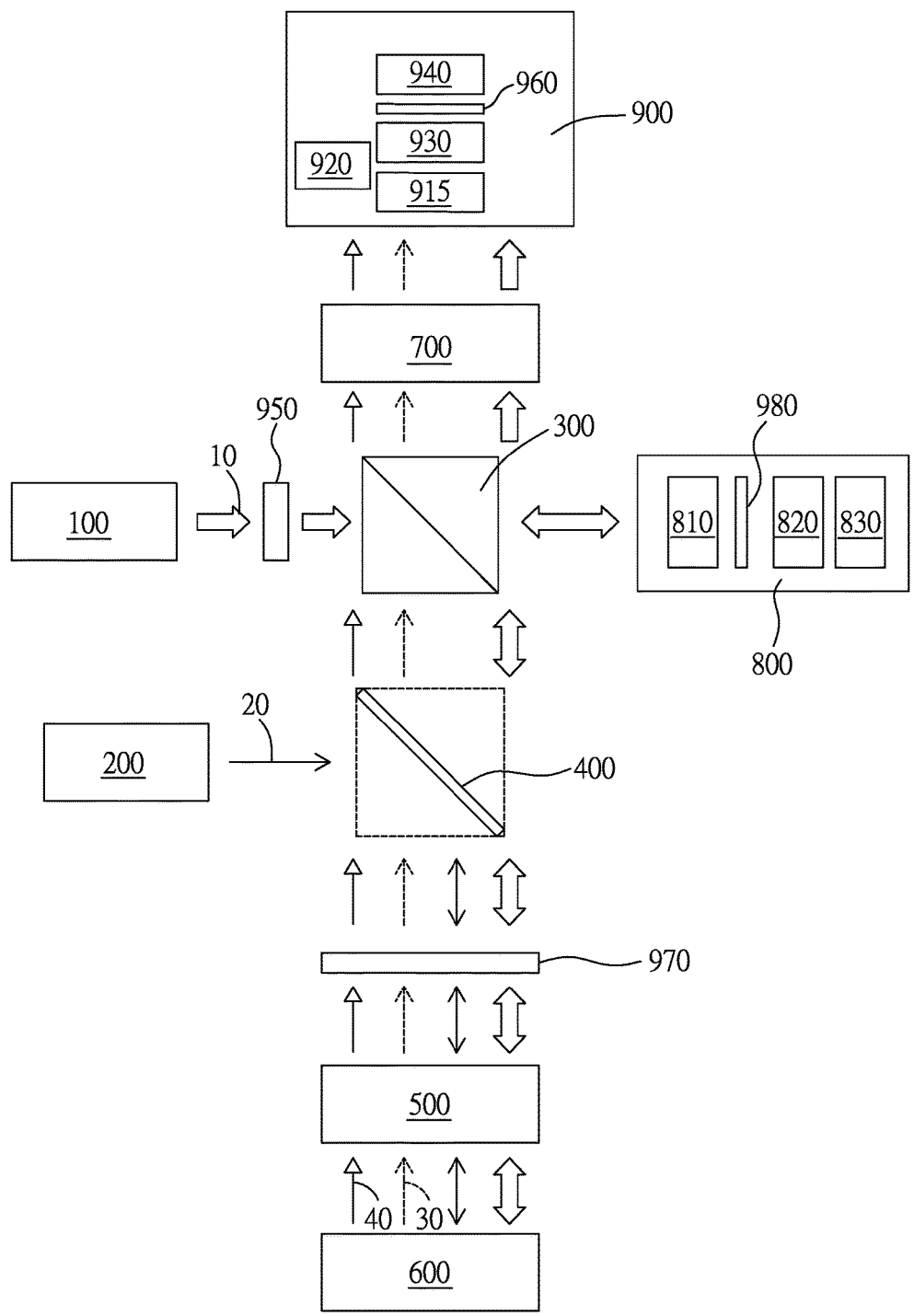
FIG. 6 illustrates a block diagram of an optical sectioning apparatus using optical interference microscopy and fluorescence microscopy according to another embodiment of the present invention.

Please refer to FIG. 6, which illustrates a block diagram of an optical sectioning apparatus using optical interference microscopy and fluorescence microscopy according to another embodiment of the present invention.

As illustrated in FIG. 6, a first polarizer 950 is disposed between the wide band light source apparatus 100 and the beam splitter 300, a second polarizer 960 is disposed in front of the two-dimensional monochrome sensing device 940, a first quarter-wave plate 970 is disposed between the first objective lens 500 and the first dichroic splitter 400, and a second quarter-wave plate 980 is disposed between the optical path delay unit 810 and the second objective lens 820.

The first polarizer 950 has a first polarization direction, the second polarizer 960 has a second polarization direction orthogonal to the first polarization direction, the first quarter-wave plate 970 has a first optical axis direction, the second quarter-wave plate 980 has a second optical axis direction, and both the first optical axis direction and the second optical axis direction are disposed within a range formed by the first polarization direction and the second polarization direction.

In one embodiment, the first polarization direction is along a vertical direction, the second polarization direction is along a horizontal direction, and both the first optical axis direction and the second optical axis direction are along a 45 degrees direction in-between the first polarization direction and the second polarization direction. When in operation, the wide band light beam 10 of the wide band light source apparatus 100 will be polarized in a vertical direction after passing through the first polarizer 950, and then split by the beam splitter 300 into a first branch and a second branch. The first branch will pass through the second quarter-wave plate 980 of the reference arm unit 800 to become a first clockwise circularly polarized light beam, which then becomes a first counter clockwise circularly polarized light beam after reflected by the reflective mirror 830, and the first counter clockwise circularly polarized light beam will become polarized in the horizontal direction after it passes through the second quarter-wave plate 980. The second branch will pass through the first quarter-wave plate 970 disposed between the first objective lens 500 and the first dichroic splitter 400 to become a second clockwise circularly polarized light beam, which then becomes a second counter clockwise circularly polarized light beam after reflected by the sample carrier unit 600, and the second counter clockwise circularly polarized light beam will become polarized in the horizontal direction after it passes through the first quarter-wave plate 970. As the second polarizer 960 in front of the two-dimensional monochrome sensing device 940 will only allow horizontally polarized light of the wide band light beam 10 to pass through, therefore, reflect light due to an antireflection film of the beam splitter 300 can be effectively blocked to further enhance an optical interference effect and promote an imaging performance.

Figure 7:
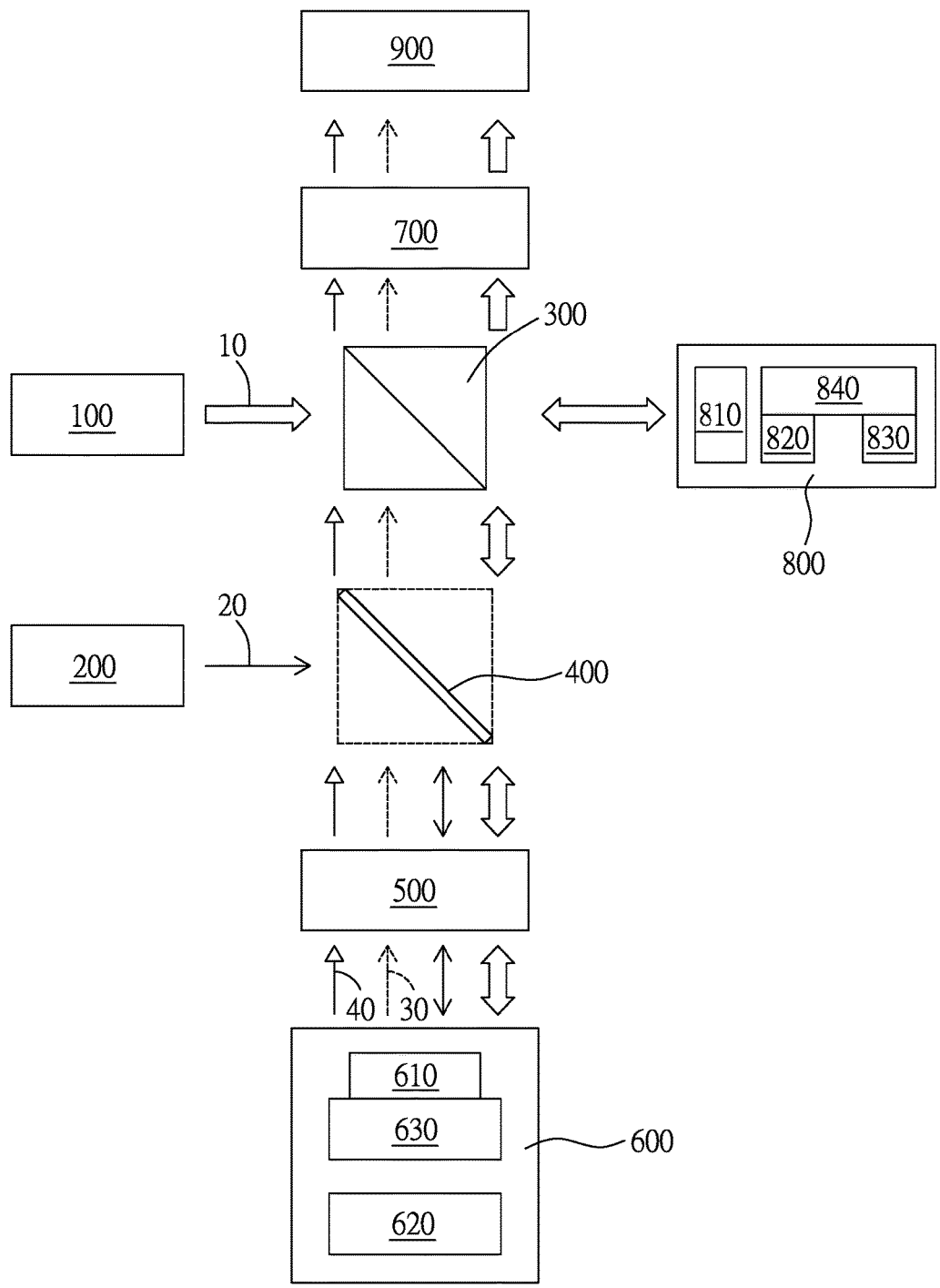
FIG. 7 illustrates a block diagram of an optical sectioning apparatus using optical interference microscopy and fluorescence microscopy according to still another embodiment of the present invention.

Please refer to FIG. 7, which illustrates a block diagram of an optical sectioning apparatus using optical interference microscopy and fluorescence microscopy according to still another embodiment of the present invention.

As illustrated in FIG. 7, the reference arm unit 800 further includes an axial motion platform 840 and the sample carrier unit 600 further includes a 3-D motion platform 630. In addition, an information processing apparatus (not shown in this figure) can be used to perform an image processing process.

By using the axial motion platform 840 to move the second objective lens 820 and the reflective mirror 830, adjusting the optical path delay unit 500, and using the 3-D motion platform 630 to move the sample 610 stained with a fluorescent dye, the information processing apparatus (not shown in this figure) can derive a 3-D image (not shown in this figure) of the sample accordingly. Since the formation process of a 3-D image is known in prior art, it will not be addressed further.

Due to the novel schemes disclosed above, the present invention possesses the advantages as follows:

1. The optical sectioning apparatus of the present invention has a first dichroic splitter disposed between a beam splitter and a first objective lens to block a short-wavelength light beam and thereby increase a relative strength of a fluorescent signal, shorten an exposure time, and speed up taking images.

2. The optical sectioning apparatus of the present invention ensures that when a fluorescent light beam emitted from a sample passes through a first dichroic splitter, since the first dichroic splitter will filter out a short-wavelength light beam, the fluorescent light beam will have a good relative strength when it passes through the first dichroic splitter, thereby shortening an exposure time and speeding up taking images.

3. The optical sectioning apparatus of the present invention has a long wavelength pass filter installed in a sensor unit to further filter out a short-wavelength light beam to increase the relative strength of a fluorescent signal, and thereby shortening an exposure time and speeding up taking images.

While the invention has been described by way of example and in terms of preferred embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

In summation of the above description, the present invention herein enhances the performance over the conventional structure and further complies with the patent application requirements and is submitted to the Patent and Trademark Office for review and granting of the commensurate patent rights.

What is claimed is:

1. An optical sectioning apparatus using optical interference microscopy and fluorescence microscopy, including:
   a beam splitter, having a first side, a second side, a third side, and a fourth side, and being capable of splitting an incident light beam received from the first side into a reflected light beam traveling out the second side and a transmitted light beam traveling out the third side;
   a wide band light source apparatus for generating a wide band light beam to be incident on the first side of the beam splitter;
   a reference arm unit, used to make the transmitted light beam travel a round trip along an adjustable optical path and then return to the beam splitter;
   a short wavelength light source apparatus for generating a short wavelength light beam;
   a first dichroic splitter, having a first side, a second side, and a third side, with the first side facing the short wavelength light source apparatus, the third side facing the second side of the beam splitter, and being capable of providing a light-blocking effect on a band of wavelengths shorter than a preset wavelength, and the short wavelength light beam having a wavelength shorter than the preset wavelength;
   a first objective lens, having a collimated side and a focal side, with the collimated side facing the second side of the first dichroic splitter;
   a sample carrier unit facing the focal side of the first objective lens and being used for carrying a sample stained with a fluorescent dye;
   a projection lens, having a light entrance side and a light exit side, with the light entrance side facing the fourth side of the beam splitter; and
   a sensor unit facing the light exit side of the projection lens.

2. The optical sectioning apparatus using optical interference microscopy and fluorescence microscopy as disclosed in claim 1, wherein the reference arm unit includes:
   an optical path delay unit, having a first side and a second side, with the first side facing the third side of the beam splitter;
   a second objective lens, having a collimated side and a focal side, with the collimated side facing the second side of the optical path delay unit; and
   a reflective mirror, facing the focal side of the second objective lens and used for reflecting the transmitted light beam, wherein the optical path delay unit is used for adjusting the adjustable optical path so that the adjustable optical path and a sample arm optical path have an optical path difference less than a coherent length, with the sample arm optical path being formed by the sample carrier unit, the first objective lens, and the first dichroic splitter.

3. The optical sectioning apparatus using optical interference microscopy and fluorescence microscopy as disclosed in claim 1, wherein both the wide band light source apparatus and the short wavelength light source apparatus are implemented with a light source, or a combination of a light source and a grating, or a combination of a light source, a grating, and a tilt-adjustable reflective mirror, or a plurality of parallel LED stripes.

4. The optical sectioning apparatus using optical interference microscopy and fluorescence microscopy as disclosed in claim 1, wherein the sample carrier unit further includes a white light source to provide a proper intensity of white light to pass through the first objective lens, the white light source including a white-light LED, a white-light halogen lamp, or a tungsten lamp.

5. The optical sectioning apparatus using optical interference microscopy and fluorescence microscopy as disclosed in claim 1, wherein the sensor unit includes a second dichroic splitter, a two-dimensional color sensing device, a long wavelength pass filter, and a two-dimensional monochrome sensing device, in which the second dichroic splitter has a first side, a second side, and a third side, with the first side facing the projection lens, and the second dichroic splitter is used to reflect a fluorescent light beam and a white light beam to and through the third side to form an image on the two-dimensional color sensing device, and to transmit a wide band light beam through the second side to form an image on the two-dimensional monochrome sensing device; or the sensor unit includes a flip-type reflective mirror, a two-dimensional color sensing device, a long wavelength pass filter, and a two-dimensional monochrome sensing device, in which the flip-type reflective mirror has a flip-on state to allow a white light beam to form an image on the two-dimensional color sensing device, and has a flip-off state to allow a wide band light beam and a fluorescent light beam to form an image on the two-dimensional monochrome sensing device, and the long wavelength pass filter can be disposed between the projection lens and the flip-type reflective mirror, or be disposed between the projection lens and the second dichroic splitter, or be disposed between the flip-type reflective mirror and the two-dimensional monochrome sensing device, or be disposed between the second dichroic splitter and the two-dimensional monochrome sensing device.

6. The optical sectioning apparatus using optical interference microscopy and fluorescence microscopy as disclosed in claim 5, wherein the wide band light beam has a wavelength range of 470 nm-800 nm, the short wavelength light beam has a wavelength range of 365 nm-460 nm, the beam splitter has an operating wavelength range of 400 nm-800 nm, and both the first dichroic splitter and the long wavelength pass filter have a cut-off wavelength range of 400 nm-470 nm.

7. The optical sectioning apparatus using optical interference microscopy and fluorescence microscopy as disclosed in claim 5, wherein the wide band light beam has a wavelength range of 650 nm-1000 nm, the short wavelength light beam has a wavelength range of 365 nm-630 nm, the beam splitter has an operating wavelength range of 400 nm-1000 nm, and all the first dichroic splitter, the second dichroic splitter, and the long wavelength pass filter have a cut-off wavelength range of 400 nm-650 nm.

8. The optical sectioning apparatus using optical interference microscopy and fluorescence microscopy as disclosed in claim 2, wherein a first polarizer is disposed between the wide band light source apparatus and the beam splitter, a second polarizer is disposed in front of the two-dimensional monochrome sensing device, a first quarter-wave plate is disposed between the first objective lens and the first dichroic splitter, and a second quarter-wave plate is disposed between the optical path delay unit and the second objective lens, wherein the first polarizer has a first polarization direction, the second polarizer has a second polarization direction orthogonal to the first polarization direction, the first quarter-wave plate has a first optical axis direction, the second quarter-wave plate has a second optical axis direction, and both the first optical axis direction and the second optical axis direction are disposed within a range formed by the first polarization direction and the second polarization direction to enhance an interference effect and promote an imaging quality.

9. The optical sectioning apparatus using optical interference microscopy and fluorescence microscopy as disclosed in claim 5, wherein a first polarizer is disposed between the wide band light source apparatus and the beam splitter, a second polarizer is disposed in front of the two-dimensional monochrome sensing device, a first quarter-wave plate is disposed between the first objective lens and the first dichroic splitter, and a second quarter-wave plate is disposed between the optical path delay unit and the second objective lens, wherein the first polarizer has a first polarization direction, the second polarizer has a second polarization direction orthogonal to the first polarization direction, the first quarter-wave plate has a first optical axis direction, the second quarter-wave plate has a second optical axis direction, and both the first optical axis direction and the second optical axis direction are disposed within a range formed by the first polarization direction and the second polarization direction to enhance an interference effect and promote an imaging quality.

10. The optical sectioning apparatus using optical interference microscopy and fluorescence microscopy as disclosed in claim 2, further including an information processing apparatus to perform an image processing process.

11. The optical sectioning apparatus using optical interference microscopy and fluorescence microscopy as disclosed in claim 10, wherein the reference arm unit further includes an axial motion platform, and the sample carrier unit further includes a 3-D motion platform, so that by using the axial motion platform to move the second objective lens and the reflective mirror, by adjusting the optical path delay unit, and by using the 3-D motion platform to move the sample stained with the fluorescent dye, the information processing apparatus can derive a 3-D image of the sample accordingly.

* * * * *